United States Patent [19]
Suzuki et al.

[11] Patent Number: 5,591,871
[45] Date of Patent: Jan. 7, 1997

[54] BISLACTONE COMPOUND AND A PROCESS FOR PRODUCING THE SAME

[75] Inventors: Naoko Suzuki, Amagasaki; Hirotoshi Nakanishi, Osaka; Kyouko Nagase, Ibaraki, all of Japan

[73] Assignee: Sumitomo Chemical Co., Ltd, Osaka, Japan

[21] Appl. No.: 520,096

[22] Filed: Aug. 28, 1995

[30]    Foreign Application Priority Data

Aug. 29, 1994   [JP]   Japan ................................... 6-203484

[51] Int. Cl.$^6$ .............................................. C07D 407/00
[52] U.S. Cl. .............................................................. 549/299
[58] Field of Search ............................................. 549/299

[56]                References Cited

U.S. PATENT DOCUMENTS

| | | | |
|---|---|---|---|
| 4,325,863 | 4/1982 | Hinsken et al. | 624/111 |
| 4,338,244 | 7/1982 | Hinsken et al. | 524/109 |
| 4,611,016 | 9/1986 | Hinsken et al. | 529/99 |

*Primary Examiner*—Amelia Owens
*Attorney, Agent, or Firm*—Birch, Stewart, Kolasch & Birch, LLP

[57]                ABSTRACT

A bislactone compound represented by the general formula (I):

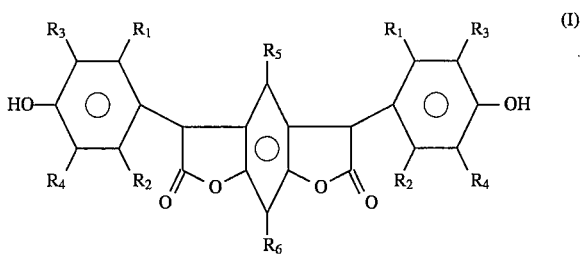

wherein $R_1$ and $R_2$ each independently represent a hydrogen atom or an alkyl group having 6 or less carbon atoms, and $R_3$, $R_4$, $R_5$ and $R_6$ each independently represent a hydrogen atom, a hydroxy group or an alkyl group having 6 or less carbon atoms, which is useful as a stabilizer for polymers and as a raw material of a positive type resist:

a process for producing the bislactone compound; and a positive resist composition comprising the bislactone compound.

5 Claims, No Drawings

BISLACTONE COMPOUND AND A PROCESS FOR PRODUCING THE SAME

The present invention relates to a novel bislactone compound which is useful as a stabilizer for polymers and as a raw material of a positive type resist e.g. for producing a planographic process plate or an integrated circuit. The present invention also relates to a process for producing the bislactone compound.

A positive type resist composition containing, as a sensitizer, a 1,2-naphthoquinonediazide sulfonic acid ester of a monolactone compound represented by the following formula:

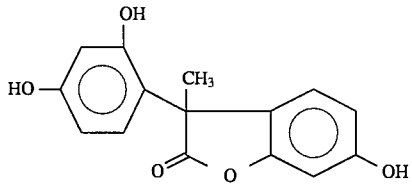

is described, for example, in JP-A-4-7735 and JP-A-5-323598.

However, a positive type resist composition made from a bislactone compound has not been known.

A bislactone compound represented by the following formula:

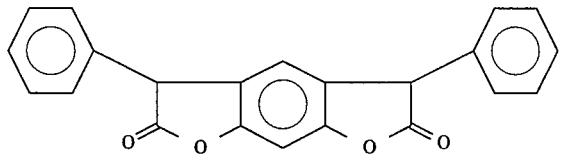

which may be used as a stabilizer for polymers, and a process for producing the same which comprises heating and reacting mandelic acid and resorcinol while distilling off by-produced water are described in Example 1 of JP-B-63-26771. However, it is difficult that the bislactone compound described in JP-B-63-26771 is used as a raw material of a positive type resist for producing a planographic process plate or an integlated circuit.

It is an object of the present invention to provide a bislactone compound which is useful not only as a stabilizer for polymers but also as a raw material of a positive type resist for producing a planographic process plate or an integrated circuit. Another object of the present invention is to provide a process for producing the bislactone compound.

The present invention thus ralates to a bislactone compound represented by the general formula (I):

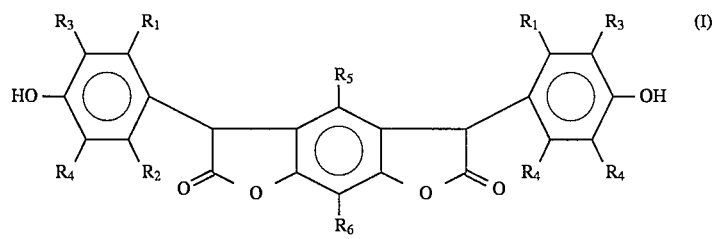

wherein $R_1$ and $R_2$ each independently represent a hydrogen atom or an alkyl group having 6 or less carbon atoms, and $R_3$, $R_4$, $R_5$ and $R_6$ each independently represent a hydrogen atom, a hydroxy group or an alkyl group having 6 or less carbon atoms.

Another subject matter of the present invention is a process for producing the bislactone compound of formula (I) which comprises allowing a 4-hydroxymandelic acid compound represented by the general formula (III):

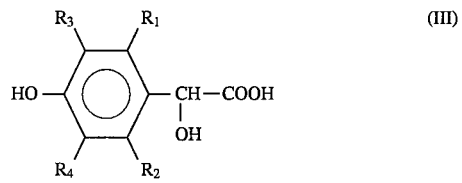

wherein $R_1$, $R_2$, $R_3$ and $R_4$ are as defined above, to react with a phenol compound represented by the general formula (IV):

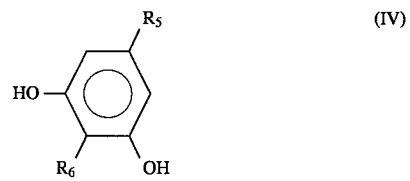

wherein $R_5$ and $R_6$ are as defined above, in the presence of an acid catalyst.

A further subject matter of the present invention is a positive resist composition comprising a bislactone compound of formula (I).

The alkyl group denoted by $R_1$, $R_2$, $R_3$, $R_4$, $R_5$ or $R_6$ in formula (I) may be a straight chain or branched chain alkyl group. As preferred examples of the alkyl, methyl and ethyl can be mentioned.

As preferred examples of the bislactone compound of formula (I), a compound represented by the general formula (II):

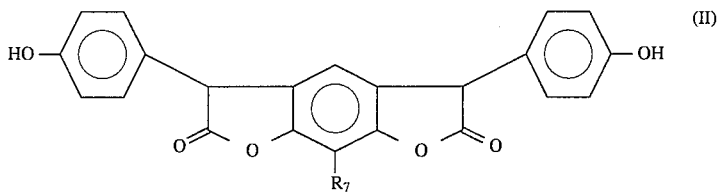

wherein $R_7$ represents a hydrogen atom or an alkyl group having 6 or less carbon atoms can be mentioned.

As preferred examples of the acid catalyst used for the reaction of a 4-hydroxymandelic acid compound of formula (III) and a phenol compound of formula (IV) to produce a bislactone compound of formula (I), inorganic acids, such as hydrochloric acid, sulfuric acid and phosphoric acid; and organic acids, such as methane sulfonic acid, trichloroacetic acid, trifluoroacetic acid and p-toluene sulfonic acid can be mentioned. In the reaction, the amount of the acid catalyst is usually 5–100 parts by weight, preferably 5–50 parts by weight, per 100 parts by weight of the 4-hydroxymandelic acid compounds of formula (III). The reaction to produce a bislactone compound of formula (I) is preferably carried out in the presence of a reaction solvent which is water or an organic solvent. Preferred examples of the organic solvent include alkyl esters of acetic acid, such as ethyl acetate and n-propyl acetate, and aliphatic cyclic ethers, such as tetrahydrofuran and dioxane. The amount of water or an organic solvent is usually 10–500 parts by weight, preferably 50–400 parts by weight, per 100 parts by weight of the phenol compounds of formula (IV).

Preferred examples of the phenol compounds of formula (IV) include resorcinol, 2-methylresorcinol, pyrogallol and 2-ethylresorcinol. In the reaction to produce a bislactone compound of formula (I), the molar ratio of the phenol compound to the 4-hydroxymandelic acid compound of formula (III) is usually 1:2–1:10, preferably 1:2–1:4.

The reaction temperature is usually in a range of 0°–100° C. The reaction time is usually in a range of 1–120 hours. After completion of the reaction, the reaction mixture is subjected to crystallization, filtration, washing, drying and, if desired, other usual methods to isolate a bislactone compound of formula (I).

Commercially available 4-hydroxymandelic acid compounds of formula (III) can be used for the process of the present invention. A 4-hydroxymandelic acid compound usable for the process of the present invention can also be obtained by reacting a 4-hydroxybenzaldehyde compound, sodium hydrogen sulfite and sodium cyanide to obtain a cyanhydrin and then hydrolyzing the cyanhydrin to obtain a oxycarboxylic acid.

The bislactone compound of formula (I) is useful not only as a stabilizer for polymer but also as a raw material of a positive type resist for producing e.g. a planographic process plate or an integrated circuit. Particularly, the bislactone compound of formula (I) is useful as a raw material of a positive type resist, because a positive type resist composition comprising
a bislactone compound of the present invention;
a 1,2-naphthoquinone-5-sulfonic acid ester of a polyhydric phenol compound (=a sensitizer); and
an alkali-soluble novolac resin which is obtained by reacting a mixture of phenol compounds containing cresol with formaldehyde in the presence of an acid catalyst, such as oxalic acid
is excellent in properties, such as sensitivity and resolution. Therefore, the positive type resist composition comprising a bislactone compound of the present invention is very desirable for producing e.g. LSI and IC.

According to the process of the present invention, the bislactone compound of formula (I) can be produced in high purity and high yield at a lower reaction temperature than the reaction temperature in the process described in Example 1 in JP-B-63-26771.

The present invention is explained in more detail with reference to the following examples. In the examples, "part" means "part by weight" unless otherwise mentioned.

EXAMPLE 1

Into a mixture of 124 parts of 2-methylresorcinol, 460 parts of water and 102 parts of p-toluenesulfonic acid, 504 parts of 4-hydroxymandelic acid was added at 60°–65° C. over 1 hour while stirring the mixture. After completion of the addition, reaction was carried out at that temperature for 20 hours. Then, 5000 parts of water was added thereto and the mixture was cooled to room temperature and was filtered to obtain a crystalline product. The crystalline product was washed with 5000 parts of water. Then the crystalline product was dissolved in a mixture of ethyl acetate and toluene in a volume ratio of 6:1, respectively, and the resulting solution was washed with water. The organic layer of the resulting mixture was then washed with water again and was concentrated to obtain an oily product. To the oily product, about twice amounts of a mixture of ethyl acetate and toluene in a volume ratio of 1:3, respectively, based on the amount of the oily product, was added and the mixture was cooled to obtain a slurry. The slurry was filtered and the crystalline product thus obtained was washed with a mixture of ethyl acetate and toluene in a volume ratio of 1:4, respectively and dried to obtain a compound represented by the following formula.

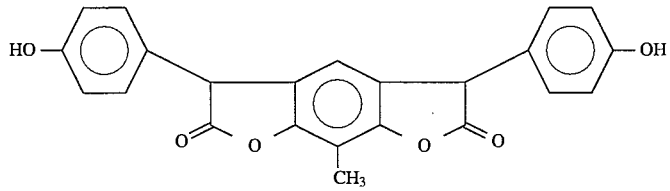

Yield is 44.3% based on 4-hydroxymandelic acid.
FD-MS (Mass spectrometry): m/e=388
Melting point: 238°–240° C.

EXAMPLE 2

A mixture of 275 parts of resorcinol, 660 parts of water, 105 parts of p-toluenesulfonic acid and 1051 parts of 4-hydroxymandelic acid was subjected to a reaction at 50°–55° C. for 28 hours while stirring the mixture, and then the reaction mixture was cooled to room temperature and was filtered to obtain a crystalline product. The crystalline product was washed with 5000 parts of water. Thereafter, the crystalline product was dissolved in 2500 parts of ethyl acetate at 60°–65° C., and the resulting mixture was filtered. The filtrate was cooled to room temperature to recrystallize the crystalline product. The crystalline product thus obtained was washed with 100 parts of ethyl acetate and was dried to obtain a compound represented by the following formula.

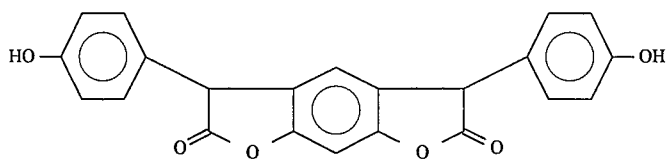

Yield is 23.5% based on 4-hydroxymandelic acid.
FD-MS (Mass spectrometry): m/e=374
Melting point: 209°–210° C.

EXAMPLE 3

Example 2 was repeated except that resorcinol was replaced with pyrogallol to obtain a bislactone compound.
FD-MS (Mass spectrometry): m/e=404

EXAMPLE 4

Example 2 was repeated except that resorcinol was replaced with 2-ethylresorcinol to obtain a bislactone compound.
FD-MS (Mass spectrometry): m/e=402

EXAMPLE 5

Example 2 was repeated except that 4-hydroxymandelic acid was replaced with 3,4-dihydroxymandelic acid to obtain a bislactone compound.
FD-MS (Mass spectrometry): m/e=390

EXAMPLE 6

Example 2 was repeated except that 4-hydroxymandelic acid was replaced with 3,4-dihydroxymandelic acid and resorcinol was replaced with 2-methylresorcinol to obtain a bislactone compound.
FD-MS (Mass spectrometry): m/e=404

EXAMPLE 7

Example 2 was repeated except that 4-hydroxymandelic acid was replaced with 3-methyl-4-hydroxymandelic acid and resorcinol was replaced with 2-methylresorcinol to obtain a bislactone compound.
FD-MS (Mass spectrometry): m/e=402

EXAMPLE 8

Through a condensation reaction of a compound represented by the following formula:

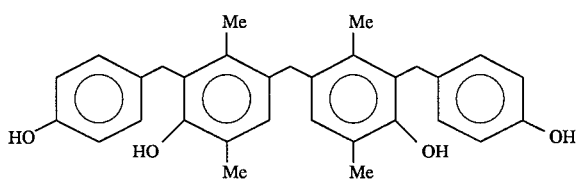

wherein Me represents a methyl group, with naphthoquinone(1,2)-diazide-(2)-5-sulfonic chloride in an mole ratio of 1:2, respectively, a photosensitizer (hereinafter denoted as "Sensitizer A") was obtained.

Through a condensation reaction of a compound represented by the following formula:

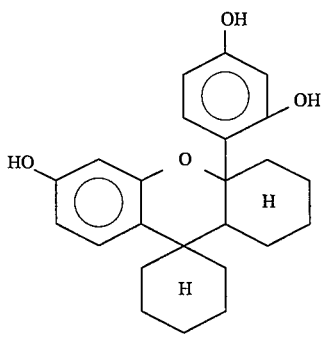

with naphthoquinone-(1,2)-diazide-(2)-5-sulfonic chloride in an mole ratio of 1:3, respectively, a photosensitizer (hereinafter denoted as "Sensitizer B") was obtained.

M-cresol, p-cresol, 2-tert-butyl-5-methylphenol and formaldehyde were reacted in an mole ratio of 50/50/2.5/66, respectively, to obtain an alkali-soluble novolac resin (hereinafter denoted as "Resin C") having weight average molecular weight of 8000 (measured by GPC, converted as polystyrene).

3.0 Parts of the bislactone compound obtained in Example 1, 5.0 parts of Sensitizer A, 1.0 parts of Sensitizer B and 11.33 parts of Resin C were dissolved in a mixed solvent consisting of 2-heptanone and γ-butyrolactone in a weight ratio of 95:5, respectively. The solution thus obtained was filtered through a filter having fine pore size to prepare a resist solution. The amount of the solvent was adjusted so that the thickness of the coated resist film after being baked became 1.07 μm.

A silicon wafer washed in a conventional manner was coated with the resist solution by means of a spin coator and it was baked on a hot plate at 90° C. for one minute. Subsequently, the wafer was exposed to light by a reduction projection exposing machine having an exposure wavelength of 365 nm (i-line) (NSR 2005i 9C, NA=0.57, manufactured by Nikon Corp.) while stepwise changing the amount of exposure. Thereafter, the wafer was baked on a hot plate at 110° C. for one minute and was developed for one minute with SOPD (developing solution; product of Sumitomo Chemical Co.,Ltd.) to obtain a positive pattern.

Sensitivity was 243.3 msec., which was exposure amount at which the film thickness became zero on a graph which was obtained by plotting the exposure amount against the retained film thickness.

γ-value was 3.08, which was obtained by plotting a normalized film thickness (=the retained film thickness/the original film thickness) against a logarithm of the exposure amount and calculating tan θ, wherein θ is the inclination of the plotted line.

Resolution was 0.34 μm, which was evaluated by measuring, with a scanning electron microscope, the dimension of the minimum line-and-space pattern which could be resolved without film thickness decrease at an exposure amount giving 1:1 line-and-space of 0.35 μm.

What we claim is:

1. A bislactone compound represented by the general formula (I):

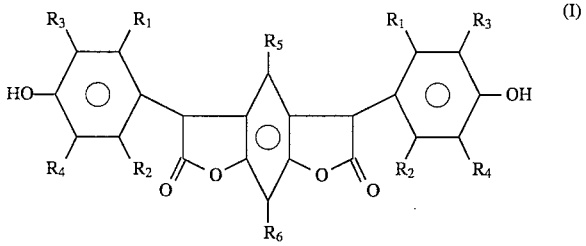

wherein $R_1$ and $R_2$ each independently represent a hydrogen atom or an alkyl group having 6 or less carbon atoms, and $R_3$, $R_4$, $R_5$ and $R_6$ each independently represent a hydrogen atom, a hydroxy group or an alkyl group having 6 or less carbon atoms.

2. A bislactone compound according to claim 1, which is represented by the general formula (II):

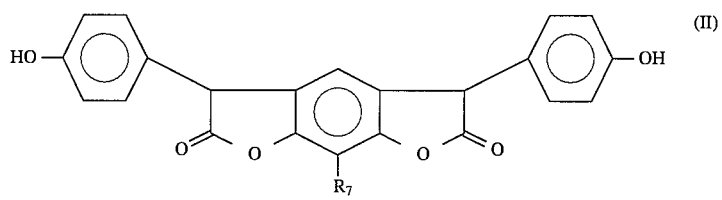

wherein $R_7$ represents a hydrogen atom or an alkyl group having 6 or less carbon atoms.

3. A process for producing the bislactone compound according to claim 1 which comprises allowing a 4-hydroxymandelic acid compound represented by the general formula (III):

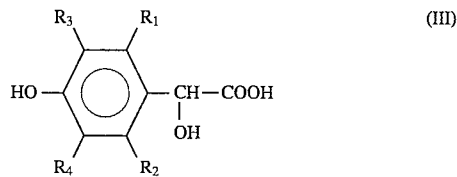

wherein $R_1$, $R_2$, $R_3$ and $R_4$ are as defined in claim 1, to react with a phenol compound represented by the general formula (IV):

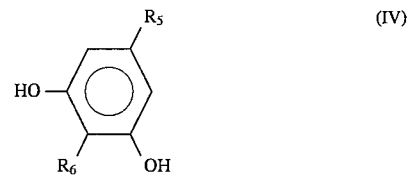

wherein $R_5$ and $R_6$ are as defined in claim 1 in the presence of an acid catalyst.

4. A process according to claim 3 wherein the reaction of the 4-hydroxymandelic acid compound and the phenol compound is carried out in the presence of water, an alkyl ester of acetic acid or an aliphatic cyclic ether.

5. A positive resist composition comprising a bislactone compound according to claim 1.

* * * * *

UNITED STATES PATENT AND TRADEMARK OFFICE
CERTIFICATE OF CORRECTION

PATENT NO. : 5,591,871
DATED : January 7, 1997
INVENTOR(S) : Naoko SUZUKI et al.

It is certified that error appears in the above-indentified patent and that said Letters Patent is hereby corrected as shown below:

Column 1, line 41, change "that" to --to use--; line 42, delete "is used"; and line 44 change "integlated" to --integrated--;

Column 2, lines 5 and 30, change "subject matter" to --embodiment--;

Column 8, at the bottom after claim 5 add the following claims:

--6. A positive resist composition comprising:
a bislactone compound according to claim 1;
a sensitizer; and
an alkali-soluble novolac resin.

7. The positive resist composition according to claim 6, wherein the sensitizer is a 1,2-naphthoquinone-5-sulfonic acid ester of a polyhydric phenol compound; and wherein the alkali-soluble novolac resin is obtained by reacting a mixture of phenol compounds containing cresol with formaldehyde in the presence of an acid catalyst.--.

Signed and Sealed this

Twentieth Day of May, 1997

Attest:

BRUCE LEHMAN

*Attesting Officer*  *Commissioner of Patents and Trademarks*